United States Patent [19]
Weiner et al.

[11] Patent Number: 5,874,225
[45] Date of Patent: Feb. 23, 1999

[54] IDENTIFICATION OF COMPOUNDS THAT MODULATE HIV-1 VPR PROTEIN ACTIVITY

[75] Inventors: David B. Weiner, Merion; David Nathan Levy, Philadelphia, both of Pa.

[73] Assignees: Trustees of The University of Pennsylvania; The Wistar Institute, both of Philadelphia, Pa.

[21] Appl. No.: 19,601

[22] Filed: Feb. 19, 1993

[51] Int. Cl.$^6$ .............................. G01N 33/53; C12Q 1/70; C07K 1/00; C07K 14/00

[52] U.S. Cl. .............................. 435/7.1; 435/5; 530/350; 530/300

[58] Field of Search .................. 435/5, 7.23, 172.1; 530/350, 300

[56] References Cited

PUBLICATIONS

Mitsuya et al., 1991, Faseb J. 5:2369–2381.
Bybee et al., 1991, Blood Rev. 5:177–192.
Scott et al., 1993, Int. J. Dev. Biol. 37:67–74.
Wiederman et al., 1993, J. Ped. Endocrin. 6:85–91.
Murphy et al., 1993, Molec. Neurobiol. 7:111–135.
Johnson, T., 1994, Pharmac. Ther. 62:247–265.
Bernardez–Clark et al., 1991, Protein Refolding, ACS, USA pp. 1–20.
Parker, C., 1990, Meth. Enzymol. 182:700–718.
Adachi, A., et al., Production of Acquired Immunodeficiency Syndrome–Associated Retrovirus in Human and Nonhuman Cells Transfected with an Infectious Molecular Clone (1986) *J. Virol.* 59:284–291.
Aguanno, S., et al., 12–0–Tetradecanoylphorbol–13–Acetate–induced Differentiation of a Human Rhabdomyosarcoma Cell Line (1990) *Cancer Res.* 50:3377–3382.
Arya, S.K., et al., Trans–Activator Gene of Human T–Lymphotropic Virus Type III (HTLV–III) (1985) *Science* 229:69–73.
Cohen, E.A., et al., Identification of HIV–1 vpr Product and Function (1990) *J. Acquir. Immune Defic. Syndr.* 3:11–18.
Cohen, E.A., et al., Human Immunodeficiency Virus vpr Product Is a Virion–Associated Regulatory Protein (1990) *J. Virol.* 64:3097–3099.
Fisher, A., A molecular clone of HTLV–III with biological activity 1985 *Nature* 316:262.
Harada, S., et al., Tumor Promoter, TPA, Enhances Replication of HTLV–III/LAV (1986) *Virology* 154:249–258.
Hattori, N., et al., The human immunodeficiency virus type 2 vpr gene is essential for productive infection of human macrophages (1990) *Proc. Natl. Acad. Sci. USA* 87:8080–8084.
Hiti, A.L., et al., Expression of the MyoD1 Muscle Determination Gene Defines Differentiation Capability but Not tumorigenicity of Human Rhabdomyosarcomas (1989) *Mol. Cell. Biol.* 9:4722–4730.
*Immonoassays for the 80's*, A. Voller et al., Eds., University Park, 1981.
Kozak, M. Point Mutations Define a Sequence Flanking the AUG Initiator Codon That Modulates Translation by Eukaryotic Ribosomes (1986) *Cell* 44:283–292.
Ling, L.L., et al., Optimization of the Polymerase Chain Reaction with Regard to Fidelity: Modified T7, Taq, and Vent DNA Polymerases, (1991) *PCR Meth. Appl.* 1:63–69.
Morgenstern and Land, Advanced mammalian gene transfer: high titre retroviral vectors with multiple drug selection markers and a complementary helper–free packaging cell line, 1990 *Nucl. Acids Res.* 18(12):3587–3596.
Ogawa, K., et al., Mutational Analysis of the Human Immunodeficiency Virus vpr Open Reading Frame, (1989) *J. Virol.* 63:4110–4114.
Osol, A., *Remington's Pharmaceutical Sciences*.
Ratner, L. et al., Complete nucleotide sequence of the AIDS virus, HTLV–III, (1985) *Science* 313:277–284.
Ratner, L. et al., Complete Nucleotide Sequences of Functional Clones of the AIDS virus, (1987) *AIDS Res. Hum. Retroviruses* 3:57–69.
Sambrook et al., *Molecular Cloning a Laboratory Manual*, Second Ed. Cold Spring Harbor Press (1989).
Shibata, R., et al. Mutational Analysis of Simian Immunodeficiency Virus From African Green Monkeys and Human Immunodeficiency Virus Type 2, (1990a). *J. Med. Primatol.* 19:217–225.
Shibata, R., et al. Mutational Analysis of the Human Immunodeficiency Virus Type 2 (HIV–2) Genome in Relation to HIV–1 and Simian Immunodeficiency Virus SIV, (1990b) *J. Virol.* 64:742–747.
Siegel and Lukas, Morphological and biochemical differentiation of the human medulloblastoma cell line TE6781, (1988) *Dev. Brain Res.* 44:269–280.
Stacich, B. et al., Characterization of Long Terminal Repeat Sequences of HTLV–III, (1985) *Science* 227:538–540.
Stratton, M.R., et al., Characterization of the human cell line TE671, (1989) *Carcinogenesis* 10:899–905.

(List continued on next page.)

*Primary Examiner*—Laurie Scheiner
*Assistant Examiner*—Jeffrey S. Parkin
*Attorney, Agent, or Firm*—Woodock Washburn Kurtz Mackiewicz & Norris, LLP

[57] ABSTRACT

The present invention is directed toward methods of identifying compounds which inhibit the human immunodeficiency virus (HIV) viral protein R (Vpr) from stimulating the differentiation of undifferentiated cells. This invention takes advantage of the observation that cell lines from rhabdomyosarcomas, which are tumors of muscle origin, have been used as models of CD4-independent HIV infection. These cell lines can be induced to differentiate in vitro. The vpr gene of HIV-1 is sufficient for the differentiation of the human rhabdomyosarcoma cell line TE671. Differentiated cells are characterized by great enlargement, altered morphology, lack of replication, and high level expression of the muscle-specific protein myosin. Morphological differentiation and inhibition of proliferation of other transformed cell lines following vpr expression was also observed. This invention also relates toward methods of identifying compounds which inhibit HIV Vpr binding to Gag. These screening methods should facilitate the identification and development of antiviral agents.

12 Claims, 6 Drawing Sheets

PUBLICATIONS

Work, T.S., et al., *Laboratory Techniques and Biochemistry in Molecular Biology*, North Holland Publishing Company, N.Y., 1978.

Wide, *Radioimmune Assay Method*, Kirkham, Ed., E. & S. Livingstone, Edinburgh, 1970, pp. 199–206.

Weiner, D.B., et al., Human Genes Other than CD4 Facilitate HIV-1 Infection of Murine Cells, (1991) *Pathobiology* 59:361–371.

Weiner, D.B., et al., Linkage of tyrosine kinase activity with transforming ability of the p185neu oncoprotein, (1989) *Oncogene* 4:1175–1183.

Wong–Staal, F., et al., Human Immunodeficiency Virus: The Eighth Gene, (1987) *AIDS Res. Hum. Retroviruses* 3:33–39.

Yu, X.F., et al. Open Reading Frame vpr of Simian Immunodeficiency Virus Encodes a Virion–Associated Protein, (1990) *J. Virol.* 64:5688–5693.

Yuan, X., et al., Human Immunodeficiency Virus vpr Gene Encodes a Virion–Associated Protein, (1990) *AIDS Res. Hum. Retroviruses* 6:1265–1271.

FIGURE 1A

NL43 vpr orf → List

DNA sequence 291 b.p ATGGAACAAGCC ... AGTAGATCCTAG linear

```
          10         20         30         40         50         60         70         80
          |          |          |          |          |          |          |          |
  1  ATGGAACAAG CCCAGAAGA CCAAGGGCCA CAGAGGGAGC CATACAATGA ATGGACACTA GAGCTTTTAG AGGAACTTAA  80
 81  GAGTGAAGCT GTTAGACATT TTCCTAGGAT ATGGCTCCAT AACTTAGGAC AACATATCTA TGAAACTTAC GGGGATACTT 160
161  GGGCAGGAGT GGAAGCCATA ATAAGAATTC TGCAACAACT GCTGTTTATC CATTTCAGAA TTGGGTGTCG ACATAGCAGA 240
241  ATAGGCGTTA CTCGACAGAG GAGAGCAAGA AATGGAGCCA GTAGATCCTA G                              291
          |          |          |          |          |          |          |
         10         20         30         40         50         60         70          80
```

FIGURE 1B

NL43 vpr orf → 1-phase Translation

DNA sequence    291 b.p.    ATGGAACAAGCC...AGTAGATCCTAG    linear

```
1/1
ATG GAA CAA GCC CCA GAA GAC CAA GGG CCA CAG AGG GAG CCA TAC AAT GAA TGG ACA CTA
 M   E   Q   A   P   E   D   Q   G   P   Q   R   E   P   Y   N   E   W   T   L
61/21                                              31/11
GAG CTT TTA GAG GAA CTT AAG AGT GAA GCT GTT AGA CAT TTT CCT AGG ATA TGG CTC CAT
 E   L   L   E   E   L   K   S   E   A   V   R   H   F   P   R   I   W   L   H
121/41                                             91/31
AAC TTA GGA CAA CAT ATC TAT GAA ACT TAC GGG GAT ACT TGG GCA GGA GTG GAA GCC ATA
 N   L   G   Q   H   I   Y   E   T   Y   G   D   T   W   A   G   V   E   A   I
181/61                                             151/51
ATA AGA ATT CTG CAA CAA CTG CTG TTT ATC CAT TTC AGA ATT GCC TGT CGA CAT ACC AGA
 I   R   I   L   Q   Q   L   L   F   I   H   F   R   I   A   C   R   H   T   R
241/81                                             211/71
ATA GGC GTT ACT CGA CAG AGG AGA GCA AGA AAT GGA GCC AGT AGA TCC TAG
 I   G   V   T   R   Q   R   R   A   R   N   G   A   S   R   S   *
                                                   271/91
```

FIGURE 1C

NL43 Vpr protein →List

| Protein | sequence | 96 | a.a | MEQAPEDQGPQR...QRRARNGASRSZ |

```
         10         20         30         40         50         60         70         80
         |          |          |          |          |          |          |          |
 1  MEQAPEDQGP QREPYNEWTL ELEELKSEA VRHFPRIWLH NLGQHIYETY GDTWAGVEAI IRILQQLLFI HFRIGCRHSR  80
81  IGVTRQRRAR NGASRS*                                                                    97
         |          |          |          |          |          |          |
         10         20         30         40         50         60         70         80
```

FIGURE 2A

NL43 p24 coding region of gag o → List

DNA   sequence    690   b.p    CCTATAGTGCAG ...    AAAGCAAGAGTT  linear

```
         10         20         30         40         50         60         70         80
         |          |          |          |          |          |          |          |
  1   CCTATAGTGC AGAACCTCCA GGGGCAAATG GTACATCAGG CCATATCACC TAGAACTTTA AATGCATGGG TAAAAGTAGT        80
 81   AGAAGAGAA GGCTTTCAGCC CAGAAGTAAT ACCCATGTTT TCAGCATTAT CAGAAGGAGC CACCCCACAA GATTTAAATA       160
161   CCATGCTAAA CACAGTGGGG GGACATCAAG CAGCCATGCA AATGTTAAAA GAGACCATCA ATGAGGAAGC TGCAGAATGG      240
241   GATAGATTGC ATCCAGTGCA TGCAGGGCCT ATTGCACCAG GCCAGATGAG AGAACCAAGG GGAAGTGACA TAGCAGGAAC      320
321   TACTAGTACC CTTCAGGAAC AAATAGGATG GATGACAAAT AATCCACCTA TCCCAGTAGG AGAAATCTAT AAAAGATGGA      400
401   TAATCCTGGG ATTAAATAAA ATAGTAAGAA TGTATAGCCC TACCAGCATT CTGGACATAA GACAAGGACC AAAGGAACCC      480
481   TTTAGAGACT ATGTAGACCG ATTCTATAAA ACTCTAAGAG CCGAGCAAGC TTCACAAGAG GTAAAAAATT GGATGACAGA      560
561   AACCTTGTTG GTCCAAAATG CGAACCCAGA TTGTAAGACT ATTTTAAAAG CATTGGGACC AGGAGCGACA CTAGAAGAAA      640
641   TGATGACAGC ATGTCAGGGA GTGGGGGGAC CCGGCCATAA AGCAAGAGTT                                      690
         |          |          |          |
         10         20         30         40         50         60         70         80
```

FIGURE 2B

NL43 GAG ORF [397 TO 1086] → 1-phase Translation

DNA sequence    1.503 b.p.    ATGGGTGCGAGA...TCGTCACAATAA    linear

```
397/1
     CCT ATA GTG CAG AAC CTC CAG GGG CAA ATG GTA CAT CAG GCC ATA TCA CCT AGA ACT TTA
      P   I   V   Q   N   L   Q   G   Q   M   V   H   Q   A   I   S   P   R   T   L
                                                        427/11
457/21
     AAT GCA TGG GTA AAA GTA GAA GAG AAG GCT TTC AGC CCA GAA GTA ATA CCC ATG TTT
      N   A   W   V   K   V   E   E   K   A   F   S   P   E   V   I   P   M   F
                                                        487/31
517/41
     TCA GCA TTA TCA GAA GGA GCC ACC CCA CAA GAT TTA AAT ACC ATG CTA AAC ACA GTG GGG
      S   A   L   S   E   G   A   T   P   Q   D   L   N   T   M   L   N   T   V   G
                                                        547/51
577/61
     GGA CAT CAA GCA GCC ATG CAA ATG TTA AAA GAG ACC ATC AAT GAG GAA GCT GCA GAA TGG
      G   H   Q   A   A   M   Q   M   L   K   E   T   I   N   E   E   A   A   E   W
                                                        607/71
637/81
     GAT AGA TTG CAT CCA GTG CAT GCA GGG CCT ATT GCA CCA GGC CAG ATG AGA GAA CCA AGG
      D   R   L   H   P   V   H   A   G   P   I   A   P   G   Q   M   R   E   P   R
                                                        667/91
697/101
     GGA AGT GAC ATA GCA GGA ACT ACT AGT ACC CTT CAG GAA CAA ATA GGA TGG ATG ACA CAT
      G   S   D   I   A   G   T   T   S   T   L   Q   E   Q   I   G   W   M   T   H
                                                        727/111
757/121
     AAT CCA CCT ATC CCA GTA GGA GAA ATC TAT AAA AGA TGG ATA ATC CTG GGA TTA AAT AAA
      N   P   P   I   P   V   G   E   I   Y   K   R   W   I   I   L   G   L   N   K
                                                        787/131
817/141
     ATA GTA AGA ATG TAT AGC CCT ACC AGC ATT CTG GAC ATA AGA CAA GGA CCA AAG GAA CCC
      I   V   R   M   Y   S   P   T   S   I   L   D   I   R   Q   G   P   K   E   P
                                                        847/151
877/161
     TTT AGA GAC TAT GTA GAC CGA TTC TAT AAA ACT CTA AGA GCC GAG CAA GCT TCA CAA GAG
      F   R   D   Y   V   D   R   F   Y   K   T   L   R   A   E   Q   A   S   Q   E
                                                        907/171
937/181
     GTA AAA AAT TGG ATG ACA GAA ACC TTG TTG GTC CAA AAT GCG AAC CCA GAT TGT AAG ACT
      V   K   N   W   M   T   E   T   L   L   V   Q   N   A   N   P   D   C   K   T
                                                        967/191
997/201
     ATT TTA AAA GCA TTG GGA CCA GCG GCT ACA CTA GAA GAA ATG ATG ACA GCA TGT CAG GGA
      I   L   K   A   L   G   P   A   A   T   L   E   E   M   M   T   A   C   Q   G
                                                        1027/211
1057/221
     GTG GGG GGA CCC GGC CAT AAA GCA AGA GTT
      V   G   G   P   G   H   K   A   R   V
```

FIGURE 2C

NL43 P24 PROTEIN → List

DNA sequence  230 a.a.  PIVQNLQGQMVH .... QGVGGPGHKARV

```
          |    10     |    20     |    30     |    40     |    50     |    60     |    70     |    80
  1    PIVQNLQGQM VHQAISPRTL NAWVKVVEEK AFSPEVIPMF SALSEGATPQ DLNTMLNTVG GHQAAMQMLK ETINEEAAEW
 81    DRLHPVHAGP IAPGQMREPR GSDIAGTTST LQEQIGWMTH NPPIPVGEIY KRWIILGLNK IVRMYSPTSI LDIRQGPKEP    160
161    FRDYVDRFYK TLRAEQASQE VKNWMTETLL VQNANPDCKT ILKALGPGAT LEEMMTACQG VGGPGHKARV                230
          |    10     |    20     |    30     |    40     |    50     |    60     |    70     |    80
```

IDENTIFICATION OF COMPOUNDS THAT MODULATE HIV-1 VPR PROTEIN ACTIVITY

FIELD OF THE INVENTION

The present invention relates to pharmaceutical compositions and methods of treating patients suffering from diseases characterized by hyperproliferating undifferentiated cells. In particular, the present invention relates to the pharmaceutical compositions comprising the HIV protein vpr or nucleic acid molecule encoding vpr and to methods of treating patients suffering from diseases characterized by hyperproliferating undifferentiated cells such as cancer by administering such pharmaceutical compositions. The present invention relates to methods of identifying compounds which have anti-HIV activity. In particular, the present invention relates to methods of identifying compounds which modulate the activity of vpr and to methods of identifying compounds which inhibit vpr binding to the HIV protein gag.

BACKGROUND OF THE INVENTION

Since the demonstration in 1987 that the small open reading frame within HIV-1 designated R encodes a 15 kd protein (Wong-Staal, F., et al., (1987) *AIDS Res. Hum. Retroviruses* 3:33–39), relatively little regarding the function of the viral protein R (vpr) has been reported. The vpr open reading frame is conserved within all genomes of HIV-1 and HIV-2 and within most, if not all, simian immunodeficiency virus (SIV) genomes. VPR is immunogenic in vivo in that a large subset of HIV$^+$individuals makes antibodies that can react with a bacterially produced vpr peptide (Wong-Staal, F., et al., (1987) *AIDS Res. Hum. Retroviruses* 3:33–39). The most direct evidence for the function of the vpr protein comes from several studies reporting that vpr increases the replication and cytopathogenicity of HIV-1, HIV-2, and SIV in primary CD4$^+$T lymphocytes and transformed T cell lines (Ogawa, K., et al., (1989) *J. Virol.* 63:4110–4114; Shibata, R., et al. (1990a). *J. Med. Primatol.* 19:217–225; and, Shibata, R., et al. (1990b) *J. Virol.* 64:742–747), although others have reported vpr has no effect on replication (Dedera, D., et al. (1989) *Virol.* 63:3205–3208). Interestingly HIV-2 mutated for vpr has been reported unable to infect primary monocyte/macrophages (Hattori, N., et al. (1990) *Proc. Natl. Acad. Sci. USA* 87:8080–8084). Transactivation of the HIV long terminal repeat and heterologous promoters by HIV is increased about 3-fold in wild-type versus vpr-negative HIV-1, though the mechanism through which vpr may transactivate transcription is unknown and may be indirect (Cohen, E. A., et al., (1990b) *J. Acquir. Immune Defic. Syndr.* 3:11–18). The relationship between the effects of vpr on promoter activity and viral infectivity is not clear. Vpr protein is incorporated into the viral particle, and this finding has led to the proposition that vpr functions early in infection, following virus penetration and uncoating, and that vpr may interact with cellular regulatory mechanisms important in the establishment of infection (Cohen, E. A., et al. 1990a *J. Virol.* 64:3097–3099; Yu, X. F., et al. (1990) *J. Virol.* 64:5688–5693.; and, Yuan, X., et al., (1990) *AIDS Res. Hum. Retroviruses* 6:1265–1271).

SUMMARY OF THE INVENTION

The present invention relates to pharmaceutical compositions that comprise HIV protein vpr and a pharmaceutically acceptable carrier or diluent.

The present invention relates to pharmaceutical compositions that comprise a nucleic acid molecule that encodes vpr and a pharmaceutically acceptable carrier or diluent.

The present invention relates to a method of stimulating undifferentiated cells to differentiated which comprises the step of contacting said cells with an amount of vpr protein sufficient to stimulate differentiation.

The present invention relates to a method of treating an individual suffering from a disease associated with hyperproliferating cells which comprises the step of administering to said individual an amount of vpr protein sufficient to stimulate differentiation of said cells.

The present invention relates to redifferentiated tumor cells.

The present invention relates to a method of treating an individual suffering from a disease associated with the loss or disfunction of cells which comprises the step of implanting into said individual redifferentiated cells.

The present invention relates to a method of identifying compounds which inhibit vpr from stimulating differentiation of undifferentiated cells which comprises the steps of first contacting, in the presence of a test compound, said cells with an amount of vpr protein sufficient to stimulate differentiation and then observing said cells to determine if cell differentiation occurs.

The present invention relates to a method of identifying compounds which inhibit vpr protein binding to gag which comprises the steps of first contacting, in the presence of a test compound, vpr protein and gag protein and then determining the level of binding.

The present invention relates to a kit for identifying compounds which inhibit vpr protein binding to gag which comprises a first container comprising vpr protein and a second container comprising gag protein.

BRIEF DESCRIPTION OF THE DRAWINGS

FIGS. 1A, 1B and 1C are the DNA sequence coding for, and the amino acid sequence for protein vpr.

FIGS. 2A, 2B and 2C are the DNA sequence coding for, and the amino acid sequence for protein gag.

DETAILED DESCRIPTION OF THE INVENTION

It has been discovered that HIV protein vpr induces undifferentiated cells to differentiate and that vpr binds to HIV protein gag. It was known that vpr is present in viral particles but its function was heretofore unknown. The ability of vpr to stimulate differentiation is believed to assist the virus in replication by producing a desirable environment particularly for production of viral particles. The presence of vpr in viral particles thus represents a means to introduce vpr protein at early stages of infection. It has been discovered that HIV protein vpr binds to HIV protein gag. This affinity allows vpr to be packaged within the viral particle during viral particle assembly. The discovery of the functional activity of vpr in infection provides for a means to induce differentiation in undifferentiated cells. Further, the discovery of vpr's activity in infection and its affinity for gag provide targets for identifying compounds with anti-HIV activity.

The discovery that vpr induces undifferentiated cells to differentiate provides for several aspects of the invention. Therapeutic aspects include use of vpr or nucleic acid molecules encoding vpr in pharmaceutical compositions useful to treat an individual suffering from diseases associated with hyperproliferating undifferentiated cells such as cancer or psoriasis.

Additionally, cells differentiated using vpr or a nuleic acid molecule that encodes vpr may be used as therapeutic cell compositions for diseases characterized by loss or malfunctioning of cells, such as Parkinson's disease. "vpr"-differentiated cells may be implanted or otherwise introduced into such individuals to provide them with functioning differentiated cells which can replace lost cells or function in place malfunctioning cells.

The discovery of vpr's activity and its affinity for gag allow for methods of screening compounds to identify compounds which may be useful as anti-HIV drugs. Assays are provided which are used to detect whether a test compound interferes with vpr's ability to stimulate undifferentiated cells to differentiate. Assays are provided which are used to detect whether a test compound interferes with vpr-gag binding. Each screen is useful to discover compounds which have anti-HIV activity by intefering with an essential activity of vpr.

One aspect of the present invention is to use vpr or nucleic acid molecule that encodes vpr in a pharmaceutical composition to combat diseases that are characterized by the hyperproliferation of undifferentiated cells such as cancer or psoriasis. According to the invention, pharmaceutical compositions are provided which comprise either vpr protein or a functional fragment thereof or a nucleic acid molecule which comprises a DNA or RNA sequence that encodes vpr protein or a functional fragment thereof. As used herein, the term "functional fragment" is meant to refer to peptides, polypeptides, amino acid sequence linked by non-peptidal bonds, or proteins which comprise an amino acid sequence that is identical or substantially homologous to at least a portion of the vpr protein amino acid sequence and which are capable of inducing a hyperproliferating undifferentiated cell to differentiate. As used herein, the term "vpr" is meant to refer to complete vpr protein or a functional fragment. The term "substantially homologous" refers to an amino acid sequence that has conservative substitutions.

One aspect of the present invention relates to pharmaceutical compositions that comprise HIV protein vpr and a pharmaceutically acceptable carrier or diluent. Pharmaceutical compositions comprising vpr protein are useful for treating an individual having a pathology or condition characterized by hyperproliferating undifferentiated cells. Pharmaceutical compositions of the present invention are particularly useful for treating cancer characterized by solid tumors. The ability to stimulate hyperproliferating undifferentiated cells to differentiate provides a means to disrupt the hyperproliferation of the cells. In diseases such as cancer and psoriasis which are characterized by the hyperproliferation of undifferentiated cells, the pharmaceutical composition is useful to stimulate the undifferentiated cells to differentiate. When hyperproliferating undifferentiated cells are induced to differentiate, they cease proliferating and eventually die.

Accordingly, another aspect of the present invention is a method of treating an individual suffering from a disease associated with hyperproliferating undifferentiated cells which comprises the step of administering to said individual an amount of vpr protein sufficient to stimulate differentiation of said cells.

Vpr may be produced by routine means using readily available starting materials as described above. The nucleic acid sequence encoding vpr as well as the amino acid sequence of the protein are well known. The entire HIV genome is published. The long terminal repeat sequences are reported in Stacich, B. et al., (1985) *Science* 227:538–540. Complete nucleotide sequences are reported in Ratner, L. et al., (1985) *Science* 313:277–284 and Ratner, L. et al., (1987) *AIDS Res. Hum. Retroviruses* 3:57–69. The DNA sequence of HIV-1/3B is published in Fisher, A., 1985 *Nature* 316:262,. The HIV-1 HXB2 strain nucleotide sequence is available on line from Genbank accession number K03455. The HIV DNA sequence is published in Reiz, M. S., 1992 *AIDS Res. Human Retro.* 8:1549. The sequence is accessible from Genbank No.: M17449. Each of these references including the publically available sequence information are incorporated herein by reference.

DNA molecules that encode vpr are readily available to the public. Plasmid pNL-43 which contains a DNA sequence encoding HIV-1 strain MN including the vpr protein and plasmid pHXB2 which contains a DNA sequence encoding HIV strain HIV-1/3B are both available from AIDS Research Reference and Reagent Program (ARRRP), Division of AIDS, NIAID, NIH, Bethesda, Md.

Provision of a suitable DNA sequence encoding the desired protein permits the production of the protein using recombinant techniques now known in the art. The coding sequence can be obtained by retrieving the DNA sequence from the publically available plasmids which comprise DNA encoding vpr protein. The DNA sequence may also be obtained from other sources of HIV DNA or can be prepared chemically using a synthesized nucleotide sequence. When the coding DNA is prepared synthetically, advantage can be taken of known codon preferences of the intended host where the DNA is to be expressed.

One having ordinary skill in the art can, using well known techniques, obtain a DNA molecule encoding the vpr protein and insert that DNA molecule into a commercially available expression vector for use in well known expression systems. For example, the commercially available plasmid pSE420 (Invitrogen, San Diego, Calif.) may be used for production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baclovirus expression system may be used for production in insect cells. The commercially available plasmid pcDNA I (Invitrogen, San Diego, Calif.) may be used for production in may be used for production in mammalian cells such as Chinese Hamster Ovary cells.

One having ordinary skill in the art can use these commercial expression vectors systems or others to produce vpr protein using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and *Pseudomonas* are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedrin promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the vpr protein produced using such expression systems.

In addition to producing these proteins by recombinant techniques, automated amino acid synthesizers may also be employed to produce vpr protein. It should be further noted that if the proteins herein are made synthetically, substitution by amino acids which are not encoded by the gene may also be made. Alternative residues include, for example, the $\omega$ amino acids of the formula $H_2N(CH_2)_nCOOH$ wherein n is 2–6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

The pharmaceutical composition comprising vpr protein and a pharmaeutically acceptable carrier or diluent may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field.

For parenteral administration, the vpr protein can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions comprising vpr protein, or fragments or derivatives may be administered by any means that enables the active agent to reach the agent's site of action in the body of a mammal. Because proteins are subject to being digested when administered orally, parenteral administration, i.e., intravenous, subcutaneous, intramuscular, would ordinarily be used to optimize absorption. In addition, the pharmaceutical compositions of the present invention may be injected at a site at or near hyperproliferative growth. For example, administration may be by direct injection into a solid tumor mass or in the tissue directly adjacent thereto. If the individual to be treated is suffering from psoriasis, the vpr protein may be formulated with a pharmaceutically acceptable topical carrier and the formulation may be administered topically as a creme, lotion or ointment for example.

The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of vpr protein can be about 1 $\mu$g to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Another aspect of the present invention relates to pharmaceutical compositions that comprise a nucleic acid molecule that encodes vpr and a pharmaceutically acceptable carrier or diluent. According to the present invention, genetic material that encodes vpr protein is delivered to an individual in an expressible form. The genetic material, DNA or RNA, is taken up by the cells of the individual and expressed. The vpr protein that is thereby produced can stimulate hyperproliferating undifferentiated cells to differentiate. Thus, pharmaceutical compositions comprising genetic material that encodes vpr protein are useful in the same manner as pharmaceutical compositions comprising vpr protein: for treating an individual having a pathology or condition characterized by hyperproliferating undifferentiated cells. Pharmaceutical compositions of the present invention are particularly useful for treating cancer characterized by solid tumors.

Thus, a further aspect of the present invention relates to a method of treating an individual suffering from a disease associated with hyperproliferating undifferentiated cells which comprises the step of administering to said individual an amount of nucleic acid that comprises a nucleotide sequence that encodes vpr protein operably linked to regulatory elements necessary for expression.

Nucleotide sequences that encode vpr protein operably linked to regulatory elements necessary for expression in the individual's cell may be delivered as pharmaceutical compositions using gene therapy strategies which include, but are not limited to, either viral vectors such as adenovirus or retrovirus vectors or direct nucleic acid transfer. Methods of delivery nucleic acids encoding proteins of interest using viral vectors are widely reported. A recombinant viral vector such as a retrovirus vector or adenovirus vector is prepared using routine methods and starting materials. The recombinant viral vector comprises a nucleotide sequence that encodes vpr. Such a vector is combined with a pharmaceutically acceptable carrier or dilluent. The resulting pharmaceutical preparation may be administered to an invidiual. Once an individual is infected with the viral vector, vpr protein is produced in the infected cells.

Alternatively, a molecule which comprises a nucleotide sequence that encodes vpr can be administered as a pharmaceutical composition without the use of infectious vectors. The nucleic acid molecule may be DNA or RNA, preferrably DNA. The DNA molecule may be linear or circular, it is preferrably a plasmid. The nucleic acid molecule is combined with a pharmacuetically acceptable carrier or dilluent.

According to the invention, the pharmaceutical composition comprising a nucleic acid sequence that encodes vpr protein may be administered directly into the individual or delivered ex vivo into removed cells of the individual which are reimplanted after administration. By either route, the genetic material is introduced into cells which are present in the body of the individual. Preferred routes of administration include intramuscular, intraperitoneal, intradermal and subcutaneous injection. Alternatively, the pharmaceutical composition may be introduced by various means into cells that are removed from the individual. Such means include, for example, transfection, electroporation and microprojectile bombardment. After the nucleic acid molecule is taken up by the cells, they are reimplanted into the individual.

The pharmacutical compositions according to this aspect of the present invention comprise about 0.1 to about 1000 micrograms of DNA. In some preferred embodiments, the pharmaceutical compositions contain about 1 to about 500 micrograms of DNA. In some preferred embodiments, the pharmaceutical compositions contain about 25 to about 250 micrograms of DNA. Most preferably, the pharmaceutical compositions contain about 100 micrograms DNA.

The pharmaceutical compositions according to this aspect of the present invention are formulated according to the mode of administration to be used. One having ordinary skill in the art can readily formulate a nucleic acid molecule that encodes vpr. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline are preferred. Stabilizers include gelatin and albumin.

Another aspect of the present invention relates to a method of stimulating undifferentiated cells to differentiate which comprises the step of contacting said cells with an amount of vpr protein or a nucleic acid molecule that encodes vpr sufficient to stimulate differentiation.

The present invention relates to cells differentiated by adminstration of vpr protein or a nucleic acid molecule that encodes vpr.

The present invention relates to to a method of treating an individual suffering from a disease associated with the loss or disfunction of cells which comprises the step of implanting into said individual redifferentiated cells.

There are a great number of diseases and disorders whose pathology is associated with lost or damaged cells. Such cells may be replaced by converting undifferentiated cells such as tumor cells or stem cells to differentiated cells which can be implanted into an individual by surgical methods.

The cells are chosen based upon their lineage; i.e. if the disease is characterized by a loss or malfunction of brain cells such as Parkinson's disease, cells of neuronal lineage such as neuronal tumor cells or neuronal stem cells are used. The undifferentiated cells are contacted in vitro with vpr protein or they are transfected with a nucleic acid molecule that comprises a nucleotide sequence that encodes vpr protein operably linked to necessary regulatory sequences which allow for expression of the nucleotide sequence in the cells. Upon differentiation, the cells are implanted into the individual by standard surgical procedures. The new differentiated cells assume the role of the lost or malfunctioning cells.

In cases where tumor cells are induced to differentiate, a safety mechanism is preferably used to insure that if the cells again become tumor cells, they can be killed. The cells may be transfected with a selective marker so that if they retransform and become tumor cells, they may be selectively killed by targeted chemotherapy. For example, a tumor cell line may be transfected with both a gene encoding vpr and a second gene encoding Herpes simplex virus thymidine kinase (tk). If, after differentiating and implantation the cells become tumor cells, administration of gancyclovir will kill the implanted cells.

A preferred embodiment of this aspect of the present invention relates to a method of treating individuals suffering from Parkinson's disease and to pharmaceutical compositions which comprises differentiated neuronal cells. According to this embodiment, publically available cultured tumor cells that are neuronal in lineage may be induced to differentiate by transfection with, on either the same nucleic acid molecule or separate molecules, a DNA sequence that encodes vpr and a DNA sequence that encodes Herpes simplex virus tk. Once differentiated, the cells are implanted into an individual suffering from Parkinson's disease.

Another aspect of the present invention relates to a method of identifying compounds which inhibit vpr from stimulating differentiation of undifferentiated cells which comprises the steps of first contacting, in the presence of a test compound, said cells with an amount of vpr protein sufficient to stimulate differentiation and then observing said cells to determine if cell differentiation occurs. It is believed that vpr's ability to stimulate undifferentiated cells to differentiate is important for the efficient production of viral particles during HIV infection. Identifying compounds which interfere with vpr's stimulation of cell differentiation provides a drug target for combatting the virus.

According to this aspect of the invention, compounds are identified which modulate vpr stimulation of differentiation of undifferentiated cells. An assay is provided which compares differentiation stimulation by vpr in the presence or absence of test compounds. Using this assay, compounds can be identified which modulate vpr stimulatory activity. In particular, compounds can be identified which inhibit vpr stimulatory action. Such compounds may be useful as anti-HIV therapeutics.

The method of the present invention comprises the step of contacting undifferentiated cells with vpr in the presence of a test compound. The cells can then be observed to determine if the vpr induces differentiation. A control may be provided in which vpr is contacted with cells in the absence of test compound. A further control may be provided in which test compound is contacted with cells in the absence of vpr. If the cells contacted with vpr in the presence of test compound do not differentiate, then anti-vpr activity is indicated for the test compound. This can be confirmed if cells contacted with vpr in the absence of test compound differentiate and the cells contacted with test compound in the absence of vpr do not differentiate.

The assay may be performed using many different types of undifferentiated cells and delivery of vpr through a variety of means. One having ordinary skill in the art, following the teachings of the Specification, can readily appreciate the several ways to practice this aspect of the present invention.

Undifferentiated cells include stem and transformed cells such as cultured tumor cells. It is preferred that the cell type chosen is one in which the differentiated form is readily distinguishable from undifferentiated cells. In some embodiments of the invention, the preferred cell types are those of the solid muscle tumor alveolar rhabdomyosarcoma such as the cell lines RD, TE671 and D17. MG63 and HOS-TE86, which are examples of osteosarcoma cell lines, may also be used. KG-1, THP-1, U937, HL60, and PLB973 cell lines are examples of myeloid lineage cells which may be used in the assay. Other cell lines that may be used in the assay include human glioblastoma cell line U-138MG, the human glioblastoma/astrocytoma cell line U373MG and the human glioblastoma/astrocytoma cell line U87-MG.

Test compound is provided, preferably in solution. Serial dilutions of test compounds may be used in a series of assays. Test compound may be added at concentrations from 0.01 $\mu$M to 1M. A preferred range of final concentrations of a test compound is from 10 $\mu$M to 100 $\mu$M.

Vpr may be delivered by a variety of means. In some embodiments of the invention, it is combined with cells as a protein. The vpr protein may be added directly to cell culture medium. Vpr protein may be produced from widely available starting materials using well known techniques, such as described above. A preferred concentration range of the vpr used is about 1 $\mu$g/ml to 1 mg/ml.

Alternatively, vpr may be contacted with undifferentiated cells by introducing into the cell a nucleic acid molecule which comprises a nucleic acid sequence encoding vpr. In such embodiments, the nucleic acid sequence may be introduced as part of an HIV particle, part of a recombinant infectious expression system particle or part of an expression vector such as a plasmid. Additionally linear DNA or RNA may also be introduced into the cell in an expressible form. One having ordinary skill in the art can construct any number of expression vectors or other nucleic molecules designed to produce vpr in cultured cells. Such an expression system may include a vector system to introduce the genetic material or the nucleic acid molecule may be introduced by other standard techniques such as transfection, electroporation or microprojectile bombardment.

Those having ordinary skill in the art can distinguish undifferentiated cells from differentiated cells routinely. Methods of distinguishing differentiated cells from undifferentiated cells include observing morpholigical, metabolic and biochemical differences between cell stages. For example, differences in size, shape and over all appearance are often profound when comparing an undifferentiated cell from a corresponding differentiated cell. Likewise, differentiation of cells results in changes in the proteins being produced by the cell.

For example, differentiated alveolar rhabdomyosarcoma cells produce high levels of myosin, a muscle protein, relative to the level of myosin produced by undifferentiated alveolar rhabdomyosarcoma cells. When undifferentiated alveolar cells are induced to differentiate, the increase in the presence of myosin may be detected using routine techniques. The means to detect the presence of a protein product are routine and include enzyme assays and ELISA assays. One having ordinary skill in the art can detect the presence or absence of a protein using well known methods.

Specifically, the initial set of cell lines which were studied included RD, TE671 and D17 as representatives of rhabdomyosarcoma (muscle) cell lines. Differentiation markers for these cells include skeletal alpha-actin, myosin, muscle specific creatine kinase, and troponin 1.

The effects of vpr on expression of the differentiated osteoblast phenotype in the osteosarcoma cell lines MG63 and HOS-TE86 can be observed using non-specific markers of alteration in cell function such as morphology and cell proliferation as well as the expression of osteoblastic markers. The osteoblast markers include the expression of mRNA's for osteocalcin, alkaline phosphatase and type I (aI) collagen (by Northern analysis) and the synthesis of osteocalcin (by radioimmunoassay) and alkaline phosphatase (colorimetric assay). The specificity of effects of test compounds on vpr are also compared to compounds effects on other established osteoblast differentiating agents such as retinoid acid and 1,25 dihydroxyvitamin $D_3$.

Differentiation analysis in cell lines KG-1, THP-1, U937, HL60, and PLB973 cell lines, which are of myeloid lineage, include increases in plastic adherence, increased phagocytosis of latex beads, positive staining for alpha-naphthyl acetate esterase and loss of expression of elastase and cathepsin G, for example. Additionally differentiation of myeloid cell lines can be correlated with changes in specific oncogene expression such as decreases in c-myc transcription.

During differentiation of glioblastoma cell lines, such as the human glioblastoma cell line U-138MG, the human glioblastoma/astrocytoma cell line U373MG and the human glioblastoma/astrocytoma cell line U87-MG, there is a decrease in cell proliferation, increases in ornithine decarboxylase, increases in GFAP, transient increases in fos, increases in specific collagen, increases in the cytoplasmic to nuclear rations, pseudopod extension, neurite outgrowth, bipolarity and activated cytoskeletal activity. Additionally, during differentiation of astrocytes increases in fibronectin expression have been reported.

The present invention relates to a method of identifying compounds which inhibit vpr protein binding to gag which comprises the steps of first contacting, in the presence of a test compound, vpr protein and gag protein and then determining the level of binding. Compounds which interfere with the binding of vpr to gag are useful to impede production of HIV particles which contain vpr. Accordingly, such compounds are useful to inhibit production of fully virulent HIV particles; therefore such compounds will be useful as anti-HIV therapeutics alone or as part of a multi-faceted anti-HIV drug regimen which includes other therapeutics.

To practice this aspect of the invention, vpr protein and gag protein are contacted in the presence of a test compound. The level of binding of the proteins is determined. The resultant level of binding is compared to the known level of binding that occurs when both proteins are contacted with each other. In the absence of a compound that inteferes with the binding, the two proteins will bind. As a control, vpr protein and gag protein are contacted in the absence of a test compound.

Test compound is provided, preferably in solution. Serial dilutions of test compounds may be used in a series of assays. Test compound may be added at concentrations from 0.01 $\mu$M to 1M. A preferred range of final concentrations of a test compound is from 10 $\mu$M to 100 $\mu$M.

Production of vpr protein is described above.

A preferred concentration range of the vpr used is about 1 $\mu$g/ml to 1 mg/ml. A preferred concentration of the vpr is about 50 $\mu$g/ml.

Gag may be produced by routine means using readily available starting materials following the teachings described above for production of vpr. One having ordinary skill in the art can, using well known techniques, obtain a DNA molecule encoding the gag protein and insert that DNA molecule into a commercially available expression vector for use in well known expression systems. One having ordinary skill in the art can, using well known techniques, isolate the gag protein produced in such expression systems.

A preferred concentration range of the gag used is about 1 $\mu$g/ml to about 1 mg/ml.

The means to detect the presence of a protein product are routine and include enzyme assays and ELISA assays. One having ordinary skill in the art can detect the presence or absence of a protein using well known methods.

One having ordinary skill in the art can readily appreciate the multitude of ways to practice a binding assay to detect compounds which modulate the binding of vpr to gag. For example, antibodies are useful for immunoassays which detect or quantitate vpr protein binding to gag protein. The immunoassay typically comprises incubating vpr protein and gag protein to allow protein-protein binding in the presence of a detectably labeled high affinity antibody capable of selectively binding to either vpr protein or gag protein, and detecting the labeled antibody which is bound to the protein. Various immunoassay procedures are described in Immunoassays for the 80's, A. Voller et al., Eds., University Park, 1981.

In this aspect of the invention, the antibody or either vpr protein or gag protein may be added to nitrocellulose, or other solid support which is capable of immobilizing proteins. The support may then be washed with suitable buffers followed by treatment with the detectably labeled TNF-specific antibody. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of antibodies may be determined according to well known methods. Those skilled in the art will be able to determine operative and optimal assay conditions for each determination by employing routine experimentation.

Positive control assays may be performed in which no test compound is added.

One of the ways in which the antibodies can be detectably labeled is by linking the same to an enzyme and use in an enzyme immunoassay (EIA), or enzyme-linked immunosorbent assay (ELISA). This enzyme, when subsequently exposed to its substrate, will react with the substrate generating a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody, it is possible to detect it through the use of a radioimmunoassay (RIA) (see, for example, Work, T. S., et al., *Laboratory Techniques and Biochemistry in Molecular Biology*, North Holland Publishing Company, N.Y., 1978. The radioactive isotope can be detected by such means as the use of a gamma counter or a scintillation counter or by autoradiography. Isotopes which are particularly useful for the purpose of the present invention are: $^{3}$H, $^{125}$I, $^{131}$I, $^{35}$S, $^{14}$C, and, preferably, $^{125}$I.

It is also possible to label the antibody with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence-emitting metals such as $^{152}$Eu, or others of the lanthanide series. These metals can be attached to the TNF-specific antibody using such metal chelating groups as diethylenetriaminepentaacetic acid (DTPA) or ethylenediamine-tetraacetic acid (EDTA).

The antibody also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isoluminol, theromaticacridinium ester, imidazole, acridinium salt and oxalate ester.

Likewise, a bioluminescent compound may be used to label the antobody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Detection of the TNF-specific antibody, fragment or derivative may be accomplished by a scintillation counter, for example, if the detectable label is a radioactive gamma emitter, or by a fluorometer, for example, if the label is a fluorescent material.

In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

As can be readily appreciated, one of the viral proteins may also be detectable and serve as a reporter molecule instead of or in addition to the antibody.

The components of the assay may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical and preferred immunometric assays include "forward" assays in which the antibody bound to the solid phase is first contacted with the one of the viral proteins to immobilize it. The second viral protein is added in the presence of the test compound. After a suitable incubation period, the solid support is washed to remove unbound protein. A second antibody is then added which is specific for the second viral protein. The second antibody is preferably detectable. After a second incubation period to permit the labeled antibody to complex with the second viral protein bound to the solid support through the unlabeled antibody and first viral protein, the solid support is washed a second time to remove the unreacted labeled antibody. This type of forward sandwich assay may be a simple "yes/no" assay to determine whether binding has occurred or may be made quantitative by comparing the measure of labeled antibody with that obtained in a control. Such "two-site" or "sandwich" assays are described by Wide, *Radioimmune Assay Method*, Kirkham, Ed., E. & S. Livingstone, Edinburgh, 1970, pp. 199–206).

Other type of "sandwich" assays are the so-called "simultaneous" and "reverse" assays. A simultaneous assay involves a single incubation step wherein the antibody bound to the solid support and labeled antibody, both viral protein and the test compound are added at the same time. After the incubation is completed, the solid support is washed to remove uncompleted proteins. The presence of labeled antibody associated with the solid support is then determined as it would be in a conventional "forward" sandwich assay.

In the "reverse" assay, stepwise addition first of a solution of labeled antibody to the viral proteins followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes may be used to construct a sensitive three-site immunoradiometric assay.

A further aspect of the present invention relates to a kit for practicing the above described method of identifying compounds which inhibit vpr protein binding to gag. This kit comprises the a first container comprising vpr protein, a second container comprising gag protein. Additionally, to practice the above defined method, means are required to distinguish vpr protein bound to gag protein from unbound vpr protein or unbound gag. In a preferred embodiment of this aspect of the invention, a third container comprising an antibody that specifically binds to either the vpr protein or gag protein is provided. At least one of the contained components, preferably the antibody, may be conjugated with an agent, such as those described above, which allows its presence to be detected. In another preferred embodiment of this aspect of the invention, a fourth container is provided which contains an antibody that specifically binds to either the vpr protein or gag protein, but not the protein which is bound by the antibody in the third container. At least one of the contained components, preferably the antibody, may be conjugated with an agent, such as those described above, which allows its presence to be detected.

While the portions of the disclosure herein which relate to theraputic compositions and methods primarily relates to therapeutics and methods of treating humans, the compositions and methods of the present invention can be applied to veterinary medical uses as well. It is within the scope of the present invention to provide methods of treating non-human as well as human individuals. Accordingly, the present invention relates to a method of treating all animals, particularly mammalian species including human, bovine, ovine, porcine, equine, canine and feline species.

EXAMPLES

Example 1

Summary

The vpr gene of HIV-1 is sufficient for the differentiation of the human rhabdomyosarcoma cell line TE671, a cell line from rhabdomyosarcomas, which are tumors of muscle origin and which can be induced to differentiate in vitro. Differentiated cells are characterized by great enlargement, altered morphology, lack of replication, and high level expression of the muscle-specific protein myosin. Morphological differentiation and inhibition of proliferation of two other transformed cell lines has also been observed. vpr-transfected cells remain fully viable in culture for extended periods.

The development of mature skeletal muscle cells entails an ordered process of cellular differentiation from muscle-committed mycocytes (presumptive myoblasts), to postmitotic myoblasts, to mature multinucleated myotubes possessing a functional muscle-contractile apparatus. Embryonal rhabdomyosarcoma is a cancer of cells resembling presumptive myoblasts and may originate from muscle satellite cells (Bruni, 1979). Rhabdomyosarcoma cell lines have been used in studies of muscle differentiation and tumorigenesis, and they can be induced to differentiate from a rapidly dividing population of cells (myoblast-like) that express low amounts of a few mature-muscle proteins to postmitotic, greatly enlarged and elongated, multinucleated (myotube-like) cells that express high amounts of mature-muscle-specific proteins and a functional muscle-contractile apparatus (Aguanno, S., et al., (1990) *Cancer Res.* 50:3377–3382; Hiti, A. L., et al., (1989) *Mol. Cell. Biol.* 9:4722–4730; Siegel, H. N., and Lukas, R. J. (1988) *Dev. Brain Res.* 44:269–280; and Stratton, M. R., et al., (1989) *Carcinogenesis* 10:899–905.)

HIV expression in a human muscle cell tumor line leads to inhibition of proliferation and activation of the suppressed endogenous cell differentiation program. The vpr gene of HIV-1 is sufficient for the observed effects and necessary for differentiation of essentially all cells. These results establish HIV-1 vpr as a regulatory protein capable of profound regulation of cell functions, including cell proliferation and differentiation.

Experimental Procedures
Cell Lines and Cultivation

The human embryonal rhabdomyosarcoma TE671 line (ATCC HTB 139) and the canine osteosarcoma D17 line (ATCC CLL 183) were obtained from the American Type Culture Collection, Rockville, Md. TE671 was originally classified as a medulloblastoma line. RD cells were provided by Dr. A. Srinivasan. All cells were grown in Dulbecco's modified Eagle's medium supplemented with 10% fetal calf serum, penicillin-streptomycin, and sodium pyruvate and maintained in a 5%–6% $CO_2$ atmosphere at 37° C.

Construction of the TE671ψ Cell Line

TE671 cells were infected with replication-defective urine retrovirus containing the human CD4 retroviral expression vector T4-pMV7 as described in Weiner, D. B., et al., (1991). *Pathobiology* 59:361–371. Clonal populations were analyzed for CD4 expression by flow cytometry as described in Weiner, D. B., et al., (1989) *Oncogene* 4:1175–1183. Briefly, cells were incubated with either Leu-3a, a murine monoclonal antibody specific for the human CD4 cell surface molecule, or Upc-21, an irrelevant isotype-matched murine monoclonal antibody. Secondary antibody was a flourescein-labeled goat anti-mouse antibody. A stable $CD4^+$ clone was selected for further analysis and designed TE671ψ

Plasmids and Cloning Strategies

The HIV-1 genomic clone pNL43 was obtained through the National Institutes of Health (NIH) AIDS Research and Reference Reagent Program, Division of AIDS, National Institute of Allergy and Infectious Diseases, NIH, (Adachi, A., et al. (1986) *J. Virol.* 59:284–291), and was used as the starting material for most of the genetic constructs used in this study. The pNL43 plasmid consists of HIV-1 proviral DNA plus 3 kb of host sequence from the site of integration cloned into pUC18.

Construction of pNLpuro

To simplify further cloning steps, the StuI site within the non-HIV 5' flanking human DNA of pNL43 was destroyed by partial digestion with StuI followed by digestion of the free ends with *Escherichia coli* polymerase. The linear plasmid was filled, then self-ligated, leaving a unique StuI site within the HIV genome. This plasmid, pNIΔstu, was then digested with the blunting enzymes StuI and BsaBI, which eliminated a large section of the coding sequence for gp120. The SV40 promoter and puromycin resistance coding region (puromycin acetyltransferase) were isolated from pBABE-puro (Morganstern, J. P., and Land, H. (1990). *Nucl. Acids Res.* 18:3587–3596; kindly provided by Dr. Hartmut Land of the Imperial Cancer Research Fund) using EcoRl and ClaI This fragment was blunted, then cloned into the StuI-BsaBI-digested pNLΔstu. A clone was selected with the SV40-puro fragment in the correct orientation so that the 3' long terminal repeat of HIV could provide poly(A) functions for the puromycin acetyltransferase message. This plasmid was designated pNLpuro.

HIV-1 Regulatory Genes

DNA encoding HIV-1 vpr protein was amplified via PCR from the HIV-1 genomic plasmid pNL43. PCR was performed under conditions that yield DNA amplification with highly fidelity (Ling, L. L., et al., (1991) *PCR Meth. Appl.* 1:63–69). Three PCR primers were used to amplify the gene. One primer, called a universal start/cloning primer (USP), encodes appropriate restriction sites for cloning the PCR product into a vector, a consensus sequence determined by Kozak, M. (1986) *Cell* 44:283–292, to promote strong initiation of translation, and an ATG start site. This primer was used in the amplification of the gene. The USP was placed in a PCR with a second short primer consisting of a reverse complement of the 3' end of the USP plus approximately 15 bp of the 5' end of the vpr gene. The double-stranded product of this PCR was used as a 5' primer in a second reaction with an appropriate 3' primer specific for the gene of interest. The 3' primer introduced restriction sites for cloning the PCR product. The sequences of the primers are as follows:

USP:ggcggctcgaggatccgccgccaccatg (SEQ ID NO:1)

vpr primer: 5' linker primer, complementary to the USP and the vpr open reading frame 5' end: ggggcttgttccatggtggc. (SEQ ID NO:2)

vpr primer: 3' cloning primer, complementary to the 3' end of the vpr open reading frame plus the BamHl cloning site: ccgcggatcctaggatctactggc. (SEQ ID NO:3)

The resulting PCR product was cloned into the retroviral vector pBABE-puro. The vector pBabe-puro, which is used as a starting material to produce many of the below listed constructs, was originally constructed and reported by Morgenstern, J. P. and H. Land, 1990 *Nucl. Acids Res.* 18(12):3587–3596, which is incorporated herein by reference. The pBabe-puro plasmid is particularly useful for expression of exogenous genes in mammalian cells. DNA sequences to be expressed are inserted at cloning sites under the control of the Moloney murine leukemia virus (Mo MuLV) long termal repeat (LTR) promoter. The plasmid contains the selectable marker for puromycin resistance. The resulting plasmid is designated pBabe–puro+vpr.

HIV regulatory genes nef, vpu and vif were amplified via PCR from the HIV-1 genomic plasmid pNL43. Primers designed to amplify the remaining regulatory genes (vif, vpu, nef) were constructed by the same design principle as employed in the amplification of vpr. Each gene was then cloned into pBabe-puro.

Cloning Strategy for Deletion of the vpr Gene from the HIV Genome

A region from just upstream of the unique PflMI site to just after the vif termination codon was amplified via PCR using primers that introduced a nonconservative amino acid change (Glu→Val) at amino acid 22 of vpr, a stop codon in the vpr reading frame immediately after amino acid 22, and an EcoRl site immediately following the new stop codon. This PCR fragment was substituted for the PflMl-EcoRl fragment of pNLpuro or pNL43. This substitution resulted in the deletion of 122 nt of the open reading frame of vpr, thus eliminating the possibility of reversion. The resulting plasmids, pNLpuroΔvpr and pNLΔvpr, encode the first 21 natural amino acids of vpr plus a valine plus all other remaining HIV-1 genes and splice junctions in their native form.

HIV-1 env-rev Plasmid

The region encoding the two exons of rev and the vpu and env open reading frames of HIV-1 HXB2 was amplified via PCR and cloned into the expression vector pCDNAl/neo (Invitrogen). Expression of rev and env proteins was demonstrated by Western blot analysis and by the ability of cells transfected with this construct to fuse with CD4+ cell lines.

tat

HIV-1 tat expression plasmid pCV1 was obtained through the Aids Research and Reference Reagent Program. A region from the vector pBABE-hygro (Morganstern, J. P., and Land, H. (1990). *Nucl. Acids Res.* 18:3587–3596) expressing hygromycin resistance was subcloned into this plasmid to make pCV1-hygro. Alternatively, pCV1 was cotransfected with PBABE-puro at a ratio of 100:1. Identical results were obtained with both methods.

Determination of Regulatory Gene Expression by Reverse Transcription PCR

TE671 cells ($0.5 \times 10^6$ to $1.0 \times 10^6$) were transfected using DOTAP (Boehringer Mannheim) with expression vectors encoding individual regulatory genes. Forty-eight hours later cells were lysed in situ using $RNA_{zag}$ (Biotecx Laboratories, Inc.), and total cellular RNA was prepared according to standard methodology. cDNA was prepared by reverse transcription using random 6-mer primers and Moloney murine leukemia virus reverse transcriptase. An aliquot of cDNA was used as a template in PCR amplification. As a control for possible genomic DNA contamination, aliquots of RNA not subject to reverse transcription were used as templates in PCR.

Analysis of HIV-1 $p24^{gag}$ Antigen Production

For analysis of the infectivity of TE671 and TE671ψ, cells were grown to 80% confluence in tissue culture flasks, then incubated with filtered (0.2 μm pore size) supernatants from HUT-78 cells chronically infected with HIV1 (strain RF). One day later cells were washed once with phosphate-buffered saline containing trypsin (2.5 mg./ml), then twice with culture medium to remove residual virus used to infect the cells. Supernatants were collected at 24 hr intervals with the first collection occurring immediately after the wash step. Detection of $p24^{gag}$ antigen was performed using an HIV1 p24 antigen assay kit (Coulter Immunology, Coulter Corporation) as per the manufacturer's instructions. This method employs an antigen-capture enzyme-linked immunosorbent assay. Wells were analyzed for absorbance at 450 nm on a Dynatech MR5000 enzyme-linked immunosorbent assay reader.

Transfections for Differentiation Studies

For differentiation experiments TE671 cells were transfected either by electroporation or with the lipid-mediated method using DOTAP. Though DOTAP produced more efficient transfections than electroporation, identical results were obtained with both methods with respect to differentiation. RD and D17 cells were transfected using DOTAP. Briefly, electroporation was performed with a Bio-Rad GenePulser and Pulse Controller on $2 \times 10^4$ to $5 \times 10^4$ cells harvested in log phase growth. DOTAP transfection was performed as per the manufacturer's instructions in tissue culture flasks on $0.5 \times 10^4$ to $1 \times 10^4$ in log phase growth. In either case selection medium was added 48–60 hr after transfection, and cells were maintained in selection for the duration of the experiments. Cells transfected with plasmids containing the puromycin resistance gene (puromycin acetyltransferase) were selected in 1 μg/ml puromycin.

Neomycin selection was in mg/ml G418.

Anti-Myosin Photomicrographic Immunofluorescence Assay

TE671 cells were transfected with the vpr expression vector, and 48 hr later the cells were trypsinized, transferred to glass slides, and selected with puromycin for 5 days prior to staining. Rapidly proliferating untransfected TE671 cells were grown on glass slides for 2–4 days before staining. Permeabilization and fixation were performed with 100% methanol at −20° C. for 10 min. The remaining steps were performed in PHEM buffer, which consists of 25 mM HEPES, 60 mM PIPES, 10 mM EGTA, and 2 mM $MgCl_2$ (pH 6.9). The fixed cells were washed three times with PHEM in between each step. Cells were first blocked with 5% normal goat serum to reduce nonspecific staining. Murine monoclonal antibody MY-32, which is specific for the myosin heavy chain of fast-twitch (type II) skeletal muscle (Sigma number M-4276), was then incubated with the specimens. As a negative control, an isotype-matched antibody (SIM.4 anti-CD4, obtained through the AIDS Research and Reference Reagent Program from Dr. James Hildreth) was used as primary antibody on some cells. Rhodamine-conjugated goat anti-mouse immunoglobulin G (TAGO) was used as secondary antibody, or alternatively a peroxidase-conjugated secondary antibody was used (Boehringer Mannheim). The cells were washed with PHEM, then examined under a fluorescence microscope and photographed.

Infection Assay

CD4+ TE671ψ or CD4− TE671 cells were plated into tissue culture at very low confluence (<5%). One day later, supernatant and infected cells were added from HIV-1 (strains RF or MN)-infected CD4+ HUT-78 T lymphoma cells. The following day the infected cells were washed from the culture, and fresh medium was added to the cells. Cells were examined for differentiation beginning on the second day after infection.

Results

Differentiation of TE671 Following Transfection with Genomic Construct pNLpuro

A drug-selectable env deletion mutant HIV-1 genomic plasmid, pNLpuro, based on the HIV-1 infectious molecular clone pNL43 was construct. pNLpuro was transfected into the human rhabdomyosarcoma cell line TE671 and selected for stable transfectants. TE671 cells normally grow as small mononuclear round or polygonal fibroblast-like adherent cells about 3–7 μm in length and developed long, sometimes branched, processes. Some cells became large, flat, and irregularly shaped. Differentiating cells often became bi- or multinucleated, though cells with long processes that resembled myotubes lacked the linear arrangement of many nuclei that is found in true myotubes. The large cells remained fully viable for several weeks.

The differentiation of TE671 cells via chemical agents is a well-described phenomenon, as this cell line has been used as a model for skeletal muscle differentiation. Some agents, including protein kinase C-activating phorbol esters, as well as serum depleted medium, will induce TE671 cells to undergo alterations in both morphology and growth characteristics that parallel in many aspects the differentiation of myoblasts into myotubes. Phorbol myristate acetate-stimulated TE671 cells increase in overall size and length, are often multinucleated, and display slowed proliferation. On the other hand, no morphologically differentiated pNLpuro-transfected cells were observed to divide when followed for up to 10 days.

Determination of HIV-1 Elements Sufficient for Differentiation

To define the viral gene(s) responsible for induction of cell differentiation in the rhabdomyosarcoma cell line, individual HIV-1 regulatory genes were examined, as some of their protein products have been reported to influence cellular events. A tat expression vector (Arya, S. K., et al., (1985) *Science* 229:69–73) was obtained and modified to permit selection of stably transfected cells. The env-rev region of HIV-1 was amplified by the polymerase chain reaction (PCR) from an HIV-1 molecular clone and subcloned directly into the pCDNAl/neo expression vector. To clone the remaining regulatory genes into expression vectors, the single open reading frame of each gene was amplified using PCR. During the PCR amplification a consensus ribosome initiation sequence was introduced immediately upstream of each start codon. The genes encoding the regulatory proteins nef, vpr, vif, and vpu were amplified by this method and subcloned into the pBABE-puro expression vector.

Each plasmid was transfected into TE671 cells and selected on the appropriate antibiotic. Expression of rev was demonstrated indirectly by showing expression of envelope protein (env) in Western blot and cell fusion assays. Since expression of env is dependent on a critical threshold level of rev expression, it can be deduced that physiologically relevant levels of rev were produced. The vpr protein expressed from the vpr vector showed a single 15 kd species by Western blot analysis. Cellular expression of tat, vif, vpr, vpu, and nef was demonstrated by reverse transcription PCR analysis. PCR products were run on 2% agarose gels and stained with ethidium bromide for photography. As a control against possible DNA carryover in the RNA preparations. RNA that was not subjected to reverse transcription was used as template in PCR.

Expression of vpu, vif, tat, nef, rev and env failed to induce significant morphological changes in TE671 cells. Vpr expression, on the other hand, induced profound differentiation in the majority of transfected cells.

To verify that TE671 differentiation involves the development of the well-defined muscle phenotype and not a novel program, vpr-transfected TE671 cells were stained with an antibody specific for the heavy chain of fast-twitch skeletal-muscle myosin, which is expressed at high levels only in mature skeletal muscle cells. Antibody MY-32 reacted strongly with vpr-transfected TE671 cells. The majority of untransfected TE671 cells expressed low levels of myosin, though, as previously reported for TE671, a few untransfected cells stained weakly for myosin. Staining with an isotype-matched control antibody was negative for both transfected and untransfected TE671 cells.

The transfection efficiency achieved by the vpr vector was equal to the efficiency of transfection of the other vectors. Transfection efficiency was determined by the number of cells remaining after selection in puromycin for 2 days, which is sufficient time to kill all nontransfected cells. After several more days, there appeared to be many fewer cells in the vpr culture than in the non-vpr cultures, owing to the continued replication of the cells in the non-vpr cultures. Not all cells transfected with either the genomic pNLpuro plasmid or with vpr alone underwent morphological differentiation, however. This result is consistent with the heterogeneous response observed in rhabdomyosarcoma lines subjected to differentiation-inducing conditions. More cells remained undifferentiated in the vpr-transfected cultures (10%–20%) than in the pNLpuro cultures (<1%). The equal transfection efficiency in the vpr culture indicates that vpr did not kill replicating cells and leave alive only the naturally occurring spontaneously differentiated cells, which could in theory produce a false interpretation that vpr can induce differentiation. The absolute number of differentiated cells in the HIV vpr-transfected cultures was always higher than that found in the other regulatory gene transfections or in untransfected TE671 cells, further indicating that vpr induced differentiation, rather than "revealing" otherwise differentiated cells. Additionally, cells of the radical phenotype observed in the HIV vpr transfected cultures were never observed in the untransfected controls or in the cells transfected with other regulatory genes.

Other cells are affected by vpr

The vpr gene was transfected into the TE671-related rhabdomyosarcoma line RD and the osteogenic sarcoma (osteosarcoma) line D17 to examine the generality of the effects observed in TE671. Following drug selection of the transfected cells, a radical alteration in size and morphology was observed in both cell lines. Inhibition of proliferation was observed in both lines. Time-lapse video microscopy of D17 cells showed them to be very active. The central or perinuclear regions of many cells rotated with a period of approximately 2 hr, frequently resulting in a distinct crescent shape. The majority of the large cells in both cultures remained viable for at least 2 weeks and did not proliferate, though some small proliferating cells remained in both the D17 and RD transfectants, as was observed in the TE671 cultures. The D17 osteosarcoma cells did not express increased levels of alkaline phosphatase, however, which is a marker for bone maturation.

Deletion of vpr from the HIV-1 Genome

Whether vpr is necessary for HIV-1-induced differentiation was next examined. To this end, a vpr deletion mutant of the HIV⁻ env plasmid pNLpuro called pNLpuroΔvpr was constructed. A stop condon was introduced after amino acid 22 of vpr, and 122 nt were removed from the coding region of vpr from amino acid 22 to amino acid 62. First, whether deletion of the vpr gene affected the expression of HIV-1 genes was tested since such an effect might complicate the interpretation of experiments. Viral protein expression following transfection with pNLpuroΔvpr was equal to expression from pNLpuro, as measured by p24$^{gag}$ protein released into the culture medium. Since expression of structural genes by HIV is dependent on successful expression of both tat and rev proteins, it is apparent that the mutation introduced into the genome did not result in a general disturbance of HIV transcription or RNA splicing. As a further control to examine the effect of deletion of vpr on HIV-1 expression, a vpr deletion mutant was constructed from wild-type pNL43, by the same method as that used for the vpr deletion mutant of pNLpuro, to yield the env⁺ construct, pNLΔvpr. When transfected into TE671ψ CD4⁺ transfectant of TE671, syncytia were efficiently produced by both the vpr⁻ and vpr⁺ constructs. Despite nearly equivalent HIV-1 protein production between pNLpuro and pNLpuroΔvpr, the outcome of transfection with the vpr deletion mutant, with respect to differentiation, was clearly different from that of transfection with the vpr⁺ HIV1 genome. While cells transfected with pNLpuro differentiated, the majority of the TE671 cells transfected with the vpr deletion mutant pNLpuroΔvpr showed either no change or a small and transient increase in size and length. Though a few myosin-staining morphologically differentiated cells were produced in each transfection, the efficiency of this effect varied from experiment to experiment and was never seen to exceed 10% of the cells remaining after drug selection. Taken together these results (summarized in Table 1) demonstrate that HIV-1-induced differentiation of TE671 cells is a function primarily of the vpr gene.

p24$^{gag}$ production in pNLpuroΔvpr continued for 2–3 weeks following transfection and subculture, whereas p24 released from pNLpuro-transfected cells was eliminated following subculture. Subculture effectively eliminated the large differentiated cells, leaving only the replicating undifferentiated cells intact. Therefore, only the differentiated cells released virus in the pNLpuro-transfection experiments. Exposure of the transfectants to the protein kinase C-activating phorbol ester phorbol myristate acetate, which has been shown to stimulate HIV-1 expression in chronically infected cells (Harada, S., et al., (1986) *Virology* 154:249–258), resulted in a 3-fold increase in p24 release from the pNLpuroΔvpr-transfected cells but no measurable p24 release from the undifferentiated pNLpuro-transfected cells. This result indicates that, in the presence of vpr, HIV-1 production in TE671 cells is incompatible with their replication, whereas in the absence of vpr, HIV1 expression can continue in replicating cells. These cells retain the ability to differentiate in response to various agents and thus remain relatively unaffected by HIV-1 expression.

Demonstration That Infection with HIV-1 Induces Differentiation

The ability of HIV infection to induce differentiation of the rhabdomyosarcoma cell line was examined. For these experiments, the cell line TE671ψ was used. TE671ψ expresses high levels of CD4 on its cell surface and can be infected with HIV at very high efficiency, resulting in a high level of viral production. Infection of TE671ψ cells at or near confluence results in cell fusion into giant multinucleated syncytia, owing to the fusion of cell membranes following coexpression of HIV envelope proteins and their receptor, CD4. To allow infection and maintenance in culture of unfused cells for several days following infection, TE671ψ was plated at low cell density, typically 5% confluence or less. Cells plated at low cell density and left unexposed to HIV-1 did not differentiate and continued to replicate. Cells infected with HIV-1 (strains RF or MN) differentiated in a manner very similar to that observed following transfection with the pNLpuro viral genome. These results demonstrate that HIV infection can directly induce cell differentiation.

Discussion

The unexpected observation that transfection of HIV-1 genomic DNA into the embryonal rhabdomyosarcoma line TE671 induced cell growth inhibition and differentiation is reported here. Infection of TE671 via a transfected CD4 molecule resulted in the same outcome, indicating that the effects did not result from transfection artifacts and have relevance to natural HIV infection. Transfection and expression of each regulatory gene of HIV-1 in the cell line revealed that the vpr gene can produce the growth inhibition and morphological differentiation that the whole virus induces. Activation of the endogenous muscle program was demonstrated by showing that the vpr-transfected cells expressed high levels of fast-twitch myosin, while the majority of untransfected cells did not. Transfection of a vpr deletion mutant into TE671 cells resulted in the production of large numbers of replicating undifferentiated cells that continued to produce high levels of viral protein. These results indicate that vpr is the primary determinant for differentiation and growth inhibition in TE671 cells. Transfection of vpr into the rhabdomyosarcoma line RD and the osteosarcoma line D17 resulted in cessation of proliferation, gross morphological changes, and profound enlargement. Thus vpr may be a regulator of cell function in cells of diverse origin.

Muscle differentiation has been well studied in rhabdomyosarcomas and in normal cells. Expression of helix-loop-helix transcription factors such as MyoD in normal myoblasts leads to differentiation into mature postmitotic myotubes. In most embryonal rhabdomyosarcomas, despite expression of MyoD, withdrawal from the cell cycle and differentiation are inhibited. Transformation of embryonal rhabdomyosarcomas is linked to expression of an activated ras oncogene, loss of a putative tumor suppressor on chromosome 11, and constitutive expression of autocrine fibroblast growth factor and transforming growth factor β. In addition, RD (and therefore TE671) has been shown to lack a wild-type p53 tumor suppressor gene. p53 expression has recently been associated with cell cycle control and the regulation of DNA repair mechanisms, cellular events linked to retroviral integration. Osteosarcomas exhibit features of bone matrix-secreting osteoblasts but are thought to arise from multipotential mesenchymal tissue and therefore to represent similarly a disregulation of primitive cells. These tumors also typically display loss-of-function p53 mutations. Vpr can at least partially overcome the block on differentiation and completely restore inhibition of cell proliferation; therefore, vpr may either replace a function lost during transformation or activate a pathway that overrides the genetic defects.

These studies directly demonstrate that the HIV-1 vpr gene encodes a protein that can function in the regulation of basic cellular events. The outcome of this regulation is observed here as an inhibition of cell proliferation and the induction of differentiation.

Example 2

A pharmaceutical composition is formulated by providing 100 $\mu g/\mu l$ pBabe–puro+vpr combined with sterile phosphate buffered saline that is isotonic with cells. The composition is administered by direct injection into a solid tumor masss of an individual.

Example 3

DNA encoding HIV-1 vpr protein is amplified via PCR from the HIV-1 genomic plasmid pNL43 using the PCR primers and strategy described in Example 1. The resulting PCR product is inserted into expression vector plasmid pSE420 (Invitrogen, San Diego, Calif.) and introduced into *E. coli*.

A pharmaceutical composition is prepared by isolating vpr protein form the cells and/or medium and combining it with a sterile pharmaceutically acceptable solution.

Example 4

DNA encoding HIV-1 vpr protein is amplified via PCR from the HIV-1 genomic plasmid pNL43 using the PCR primers and strategy described in Example 1. The resulting PCR product is inserted into expression vector plasmid pYES2 (Invitrogen, San Diego, Calif.) and introduced into *S. cerevisiae*.

A pharmaceutical composition is prepared by isolating vpr protein form the cells and/or medium and combining it with a sterile pharmaceutically acceptable solution.

Example 5

DNA encoding HIV-1 vpr protein is amplified via PCR from the HIV-1 genomic plasmid pNL43 using the PCR primers and strategy described in Example 1. The resulting PCR product is inserted into expression vector plasmid pcDNA I (Invitrogen, San Diego, Calif.) and introduced into Chinese Hamster Ovary (CHO) cells.

A pharmaceutical composition is prepared by isolating vpr protein form the cells and/or medium and combining it with a sterile pharmaceutically acceptable solution.

Example 6

Recombinant vpr protein was produced in baculovirus. Production of recombinant vpr protein allowed for studies of the function of the protein in vitro, permitted the generation of anti-vpr antibodies in rabbits and monoclonal antibodies in mice.

The vpr gene was cut out of the vpr-pBabe-puro construct. This insert was then introduced into the baculovirus expression vector pVL-1393 (PharMingen) by standard techniques. Recombinant viruses were produced as previously described (Matsuura, et al., *J. Gen. Virol.* 1987, 68:1233–1250) using Baculogold (PharMingen) linearized DNA in cotransfection experiments into *Spodoptera fungupeida* (SF-9) cells. SF-9 cells and the subsequent viral infections were carried out as previously described (Matsuura et al. 1987, Id.; O'Reilly, et al., *Baculovirus Expression Vectors, A Laboratory Manual*, H. Freeman Press, N.Y., N.Y. 1991). The presence of recombinant virus was easily observed under the light microscope following transfection. The presence of vpr protein was tested by Enzyme linked immuno-sorbent assay (ELISA) and western Blot analysis, using a rabbit anti-peptide (amino acids 2–21 N-terminus) polyclonal serum obtained through the AIDS repository.

Sf-9 cells were infected with recombinant virus at a multiplicity of infection of 5–10 and harvested at various times post infection. Whole cell and supernatant fractions were analyzed by ELISA using the aforementioned antibody. As early as 24 hours post infection, recombinant protein could be found in the supernatant. This presence would reach its peak at 30 hrs. post infection. Fractionation experiments were undertaken to optimize the collection of vpr protein. The majority of the vpr reactivity was found to be located in supernatant of recombinant Sf-9 cells. Little additional vpr protein was recovered from nonionic detergent lysates of cell sonicates.

The activity of this protein was further verified by screening the protein containing cell culture supernatant with a mixture of HIV+ seropositive patient samples as well as control samples. HIV patients have been reported to produce an humoral immune response to the vpr gene product. Immulon II ELISA plates (Dynatech laboratories, Chantilly, Va.) were coated with three dilutions of the vpr supernatant. These were then probed with 2 serial dilutions of heat inactivated patient sera. Our results demonstrate that HIV positive patient sera did react with the vpr present in the cell supernatant. The level of their reactivity was not correlated to the levels of reactivity the sera contained against the HIV-1 envelope (as measure by solid phase ELISA).

Rabbit anti-vpr protein was titrated to 1/1000 dilution and used in ELISA assay to determine production of vpr by various Sf-9 cell preparations. Specific and significant reactivity was observed in supernatant fraction from vpr transfected cells only. The rabbit antisera is an epitope restricted anti-peptide antisera and as such may not recognize a poorly processed insoluble cell associated vpr fraction in these cells. To confirm vpr production the identical samples were reacted with pooled HIV patient sera and pooled normal human sera was used as a specific control. HIV positive patient sera reacted with the supernatant containing fraction in a similar manner to the rabbit antisera. These same sera samples reacted very poorly with supernatants from non-infected Sf-9 cells. The same patient sera reacted poorly with supernatants from Sf-9 cells which were infected with control recombinant viruses (viruses which were formed by cotransfecting linearized DNA and pVL 1393 alone). The reactivity observed demonstrates the production of vpr protein in the supernatants of Sf-9 infected cells.

The vpr protein containing supernatant was subjected to purification by two different chromatography methods.

Supernatants from infected Sf-9 cells were concentrated in an amicon pressure filter unit, dialyzed, clarified and treated with protease inhibitors prior to column chromatographyThe 24 hour vpr product in the supernatant was concentrated, centrifuged at 10000 g for 10 min. Protease inhibitor were then added to this supernatant (PMSF, aprotonin, leupeptin and EDA) at their appropriate concentrations. This solution was then passed over a protein A-rabbit anti-vpr column. Rabbit anti-vpr immunoglobulin was purified on a protein A-agarose column and eluted and dialyzed and then coupled to CNBr-sepharose 4B beads according to the manufacturers instructions (Sigma). This column was then utilized for immunoaffinity chromatography of baculovirus vpr. Vpr was eluted in a pH gradient. The column was then washed with PBS. 10 mM Na-Phosphate, ph 8.0, and elution by a pH gradient was undertaken. Specific reactivity appeared to be concentrated over a limited fraction number as determined by rabbit anti-vpr antisera reactivity in ELISA. The specific protein peak and activity peak clearly overlap.

In addition, vpr protein was collected off a DEAE sepharose column using a salt gradient. Baculovirus-vpr protein containing supernatant was treated as above and then placed over a DEAE-sepharose column. The column was eluted by salt gradient, vpr activity was concentrated over a limited range.

Both purification procedures generate samples which react with HIV patient samples as well as the rabbit anti-vpr peptide antisera in ELISA and in western blotting experiments. In western blotting experiments, a 26 Kd protein is present a dominant 14 Kd protein and two small protein bands suggestive of breakdown products are observed. The 26 Kd band may represent an artifact of purification (such as acetylation) or may indicate a state of aggregation requiring further investigation.

Example 7

DNA encoding HIV-1 vpr protein was amplified via PCR from the HIV-1 genomic plasmid pNL43 using the PCR primers and strategy described in Example 1. The resulting PCR product is inserted into expression vector plasmid of the MaxBac™ (Invitrogen, San Diego, Calif.) complete baclovirus expression system and introduced into insect cells used in that system.

A pharmaceutical composition is prepared by isolating vpr protein form the cells and/or medium and combining it with a sterile pharmaceutically acceptable solution.

Example 8

Glioblastoma cell lines were tranfected with the vpr expression vector and specific examples of differentiation events were observed. For differentiation experiments the cells were transfected either by a lipid-mediated method using DOTAP (Boehringer Mannheim). DOTAP (Boehringer Mannheim) transfection was performed per the manufacturer's instructions in tissue culture flasks on 0.5–1×10$^6$ cells in log phase growth. Selection medium was added 48–60 hours post transfection and cells were maintained in selection for the duration of the experiments. Cells transfected with plasmids containing the puromycin resistance gene (PAC) were selected in 1 µg/ml puromycin (Sigma) For both the cell lines U87-MG and U138 MG specific morphological differentiation was observed. In comparison to control transfected cells the vpr transfected cells exhibited extended pseudopods and demonstrated neurite outgrowth concurrent with an observed inhibition of their cellular proliferation. Both cell lines also demonstrated an increased cytoplasmic to nuclear ratio as well as a clear enlargement in cell size. Frequent bipolarity was also observed in the vpr transfected cell lines along with active cytoskeletal activity.

Test assays comprise the steps of adding test compound to the to the medium used in the cell cultures. Test compound is provided in 10 dilutions ranging from 10 $\mu$M to 100 $\mu$M.

A control assay may optionally be run comprising the step of adding vpr protein to cells without adding test compound.

Analysis of non-specific and lineage specific markers in these cell lines is performed 2 to 14 days post transfection.

Example 9

A screen for identifying compounds which inhibit vpr's ability to induce differentiation of undifferentiated cells is performed as follows.

Either the human embryonal rhabdomyosarcoma TE671 line (ATCC HTB 139) and the canine osteosarcoma D17 line (ATCC CLL 183) are used. The cells are maintained in appropriate cell culture medium under standard conditions.

Vpr is produced as described in Examples 3, 4, 5 or 6.

Test assays comprise the steps of contacting the cells with vpr in the presence of a test compound. A mixture of vpr and the test compound are added to the cell culture medium together or separately. Test compound is provided in 10 dilutions ranging from 10 $\mu$M to 100 $\mu$M.

A control assay may optionally be run comprising the step of adding vpr protein to cells without adding test compound.

After 2–14 days, cells are observed to determine whether differentiation has occurred. Morphological and size changes indicating differentiation are described in Example 1. Visual observation may be accompanied by or substituted with an antibody assay to observed whether myosin is being produced by the cells. Anti-myosin assay is performed as described in Example 1.

Example 10

A simple in vitro ELISA based system for mapping interaction sites between vpr and gag. Baculovirus produced vpr as outlined above and baculovirus gag produced by similar means were used in binding assays. ELISA plates were coated with gag or vpr and reacted with specific antisera as controls, or coated with dilutions of gag protein followed by vpr and sandwiched with anti-vpr antibodies. Alternatively, plates were coated with dilutions of vpr followed by gag protein and sandwiched with anti-gag specific antisera. Controls for specificity include that gag antisera does not react with vpr, vpr antisera does not react with gag, neither gag nor vpr antisera reacts with BSA. Plates were coated with recombinant antigen in carbonate buffer, washed extensively, blocked with PBS/1% BSA and then washed extensively, secondary protein was dissolved in PBS/BSA and incubated at 4 C. 1 hr, then washed extensively and reacted with specific antisera. Specific sandwich activity was detected in both directions as described above.

Example 11

Using PCR and recombinant DNA technology, truncation mutants of the vpr gene were constructed and cloned into PBABE expression plasmids. These constructs delete vpr in approximately 20AA groups from the carboxy terminus traveling in toward the amino terminus of the protein. The resulting protein products are 72AA, 50AA and 30AA.

Preliminary studies indicate that the carboxyl terminus 24AA of vpr is necessary for induction of differentiation of both the rhabdomyosarcoma and glial cell lineages as loss of the inhibition of proliferation and loss of morphological changes with the deletion mutants has been observed. One interesting observation of these studies is that this carboxy region contains a significant region of homology with the muscle oncogne ski. The avian retroviral oncogene ski shows properties resembling those described for vpr (Colmenares and Stavnezer, *Cell,* 1989).

Studies suggest that carboxy terminal deletion vpr mutants still retain gag binding activity in this system. This assay therefore differentiates the functional region of vpr which interacts with gag and the functional region for cell differentiation function.

TABLE 1

HIV-1 Constructs Used in Example 1

| Contruct | Vector or Derivation | vpr | Differentiation | p24 Production | Characteristics |
|---|---|---|---|---|---|
| pNLpuro | HIV1 pNL43 | + | +++ | +++ | env deletion mutant |
| vpr | pBABE-puro | + | +++ | N/A | |
| vif | pBABE-puro | – | – | N/A | |
| vpu | pBABE-puro | – | – | N/A | |
| nef | pBABE-puro | – | – | N/A | |
| tat | pCV-1 | – | – | N/A | |
| env-rev | pcDNA1/neo | – | – | N/A | env⁺, syncytia:++ |
| pNLpuroΔvpr | pNL43 | – | –/+ᵃ | +++ | env, deletion mutant |
| pNL43 | pNL43 | + | NT | +++ | env⁺, syncytia in TE671ψ:++ |
| pNLΔvpr | pNL43 | – | NT | +++ | env⁺, syncytia in TE671ψ:++ | p24 release into the culture medium was measured 48 hr following transfection, as described in Experimental Procedures.
ᵃTransient increase in size in some cells, with reversion of phenotype observed after approximately 6 days, and differentiation in a small subset (5%–10%)
NT, not tested; N/A, not applicable.

We claim:

1. An in vitro method of identifying compounds that are capable of inhibiting HIV-1 Vpr-mediated differentiation of undifferentiated cells comprising the following steps:
(I) contacting undifferentiated cells with HIV-1 Vpr in the presence or absence of a test compound; and,
(ii) determining whether said cells cease proliferating and display cellular differentiation markers in the presence or absence of a test compound;
wherein the presence of cellular proliferation and absence of differentiation markers in the test sample is indicative of said compound being capable of inhibiting HIV-1 Vpr-mediated differentiation of undifferentiated cells.

2. The method of claim 1 wherein said undifferentiated cells are selected from the group consisting of: solid muscle tumor alveolar rhabdomyosarcoma cell line RD, solid muscle tumor alveolar rhabdomyosarcoma cell line TE671, osteosarcoma cell line D17, osteosarcoma cell line MG63, osteosarcoma cell line HOS-TE86, myeloid lineage cell line KG-1, myeloid lineage cell line THP-1, myeloid lineage cell line PLB973, human glioblastoma cell line U-138MG, human glioblastoma/astrocytoma cell line U373MG, and human glioblastoma/astrocytoma cell line U87-MG.

3. An in vitro method of identifying compounds that are capable of inhibiting HIV-1 Vpr-mediated suppression of cellular proliferation comprising the following steps:
(I) contacting proliferating cells with HIV-1 Vpr in the presence or absence of a test compound; and,
(ii) determining whether said cells cease proliferating in the presence or absence of said test compound;
wherein the presence of cellular proliferation in the test sample is indicative of said compound being capable of inhibiting HIV-1 Vpr-mediated suppression of cellular proliferation.

4. The method of claim 3 wherein said proliferating cells are selected from the group consisting of: solid muscle tumor alveolar rhabdomyosarcoma cell line RD, solid muscle tumor alveolar rhabdomyosarcoma cell line TE671, osteosarcoma cell line D17, osteosarcoma cell line MG63, osteosarcoma cell line HOS-TE86, myeloid lineage cell line KG-1, myeloid lineage cell line THP-1, myeloid lineage cell line PLB973, human glioblastoma cell line U-138MG, human glioblastoma/astrocytoma cell line U373MG, and human glioblastoma/astrocytoma cell line U87-MG.

5. An in vitro method for the identification of compounds capable of inhibiting HIV-1 Vpr binding to HIV-1 Gag comprising the following steps:

(I) contacting, in the presence or absence of a test compound, HIV-1 Vpr and Gag; and (ii) determining the level of binding between HIV-1 Vpr and Gag, wherein a reduction in binding in the presence of the test compound is indicative of said compound being capable of inhibiting HIV-1 Vpr binding to Gag.

6. The method of claim 5 wherein said binding level is determined by the addition of a labeled antibody.

7. The method of claim 5 wherein said HIV-1 Vpr and Gag are produced in eukaryotic cells.

8. The method of claim 5 wherein said HIV-1 Vpr and Gag are produced in insect cells.

9. The method of claim 5 comprising the following steps:

(I) contacting, in the presence or absence of a test compound, eukaryotically expressed HIV-1 Vpr and Gag, wherein said Vpr is attached to a solid support;

(ii) washing the mixture of step (I) to remove unbound Gag protein; and, (iii) determining the level of binding between HIV-1 Vpr and Gag through the addition of a Gag-specific labeled antibody, wherein a reduction in binding in the presence of the test compound is indicative of said compound being capable of inhibiting HIV-l Vpr binding to Gag.

10. The method of claim 9 wherein said HIV-1 Vpr and Gag are produced in insect cells.

11. The method of claim 5 comprising the following steps:

(I) contacting, in the presence or absence of a test compound, eukaryotically expressed HIV-1 Vpr and Gag, wherein said Gag is attached to a solid support;

(ii) washing the mixture of step (I) to remove unbound Vpr protein; and, (iii) determining the level of binding between HIV-1 Vpr and Gag through the addition of a Vpr-specific labeled antibody, wherein a reduction in binding in the presence of the test compound is indicative of said compound being capable of inhibiting HIV-1 Vpr binding to Gag.

12. The method of claim 11 wherein said HIV-1 Vpr and Gag are produced in insect cells.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GGCGGCTCGA GGATCCGCCG CCACCATG                                      2 8

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GGGGCTTGTT CCATGGTGGC                                          2 0

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCGCGGATCC TAGGATCTAC TGGC                                    2 4